US006219575B1

(12) United States Patent
Nemati

(10) Patent No.: US 6,219,575 B1
(45) Date of Patent: Apr. 17, 2001

(54) METHOD AND APPARATUS TO ENHANCE OPTICAL TRANSPARENCY OF BIOLOGICAL TISSUES

(76) Inventor: Babak Nemati, 5313 Town Ct. South, Lawrenceville, NJ (US) 08876

( * ) Notice: Subject to any disclaimer, the term of this patent is extended or adjusted under 35 U.S.C. 154(b) by 0 days.

(21) Appl. No.: 09/177,348

(22) Filed: Oct. 23, 1998

(51) Int. Cl.[7] .............................. A61N 1/30; A61M 31/00; A61B 19/00
(52) U.S. Cl. .............................. 604/20; 604/500; 128/898
(58) Field of Search ................................ 604/20, 19, 21, 604/500, 506, 507, 511; 128/898

(56) References Cited

U.S. PATENT DOCUMENTS

| | | | |
|---|---|---|---|
| 4,802,748 | 2/1989 | McCarthy et al. | 350/507 |
| 5,019,034 | 5/1991 | Weaver et al. | 604/20 |
| 5,772,587 | * 6/1998 | Gratton et al. | 600/310 |
| 5,817,153 | * 10/1998 | Pendl et al. | 8/94.11 |

OTHER PUBLICATIONS

Vargas et al., "Use Of An Agent To Reduce Scattering In Skin", Lasers in Surgery and Medicine 24:133–141 (1999).*
Lucas, "The Architecture of Living Cells, etc.", Apr. 28, 1930, Bell Telephone Laboratories pp. 599–607.
Chan, et al., "Chemically Enhanced Scleral Transmission, etc.", 1996, Proceedings of the Fourteenth Annual Houston Conference on Biomedical Engineering Research , Abstract.
Chandrasekhar, "Radiative Transfer", 1960, pp. 1–13. Vogel et al, "Optical Properties of Human Sclera, and Their Consequences for Transscleral Laser Applications", 1991, Laser Surg Med, 11(4) pp. 331–340.
Cantor et al. "Neodymium–YAG Transscleral Cyclo–photocoagulation", 1989, Investigative Ophthalmology And Visual Science, 30 (8), pp. 1834–1837. Flood et al. "Hyperosmotic Agents", Duane's Biomedical Foundations of Ophthalmology, vol. 3, p. 5.
Prausnitz et al., "Reversible Skin Permeabilization for Transdermal Delivery of Macromolecules", 1998, Crit Rev Ther Drug Carrier Syst. 14(4) pp. 455–483.
Kost et al, "ElectronicallyControlled Drug Delivery", 1998, pp. 215–228.
Manolis et al., "Radiofrequency Catheter Ablation for Cardiac Tachyarrhythmias", 1998, Annals of Internal Medicine, 121(6), pp. 452–461.
Henry et al. "Microfabricated Needles; a Novel Approach to Transdermal Drug Delivery", J. Pharm. Sci 87(8) pp. 922–925.

* cited by examiner

*Primary Examiner*—Richard K. Seidel
*Assistant Examiner*—Michael J Hayes
(74) *Attorney, Agent, or Firm*—Jack Schuman

(57) ABSTRACT

Method and apparatus for enhancing the optical transparency of biological tissue covered by a surface permeability barrier of tissue, involving the delivery of a clarifying agent to the target biological tissue to alter the attenuation characteristics of the target biological tissue.

20 Claims, 12 Drawing Sheets

METHOD AND APPARATUS TO ENHANCE OPTICAL TRANSPARENCY OF BIOLOGICAL TISSUES

BACKGROUND OF INVENTION

The present invention relates to modifying the optical properties of tissue on a transient basis, and more particularly, it relates to a method and apparatus for delivery of a chemical agent to a target tissue, in order to increase the optical transmission through this tissue, on a transient basis.

It is believed that the administered chemical agent displaces the aqueous interstitial fluid of the tissue, thereby effectively altering the interstitial refractive index of the tissue. If the index of refraction of the administered chemical is closer to that of the other components of the tissue, the introduction of this chemical will result in a reduction in the heterogeneity of the refractive indices of the tissue, which in turn reduces the level of scattering within the tissue. Since optical attenuation through the tissue is primarily due to absorption and scattering, a substantial change in scattering dramatically affects the optical attenuation characteristics of most biological tissues.

Previous patents and disclosures relating to the field of this invention have focused on the use of a topical chemical agent for index matching at the tissue-air interface (these prior patents and disclosures are fully identified under the heading "References" at the end of the specifications). For instance, McCarthy, et al. (McCarthy, Fairing, & Buchholz, 1989), disclose the use of an immersion medium (such as glycerol, water, or oil) to match the refractive index of the tissue specimen with that of an objective lens used in their confocal microscope. This approach serves to minimize or eliminate specular reflection, which accounts for approximately 3–4% of loss, when light is irradiated on a tissue-air interface. This approach is well known to one skilled in the art, and Lucas, et al., disclose a similar method as early as 1930 (Lucas, 1930).

The present invention is distinct from the prior art in that it changes the scattering properties of biological tissues, underlying the surface permeability barrier of tissue covering the said biological tissue, by changing the refractive index of the interstitial fluid within the stroma and the entire volume of the covered biological tissue. While topical administration of immersion fluids affects the optical transmission through biological tissues by only 3–4%, the present invention can improve light transmission through biological tissues by up to five or six hundred percent.

The only prior art known to the inventor which teaches enhancement of tissue transparency by topical administration of chemicals is an abstract authored by Chan, et al., and the inventor, in the Fourteenth Annual Houston Conference on Biomedical Engineering Research (Chan, Nemati, Rylander, & Welch, 1996). This abstract teaches the efficacy of this approach for enhancing the transparency of porcine scleral tissue, in order to perform transscleral cyclophotocoagulation on glaucomatous eyes. However, this abstract does not teach bypassing of the most superficial tissue layer (e.g., stratum corneum, for skin, and conjunctiva, for sclera), in order to administer the topical clarifying agents. Without bypassing the outer-most tissue layer, the underlying target tissue layers are impermeable, and the chemicals administered topically to the outermost tissue layer will not reach the interstitial space of the tissue, and therefore will have no impact on the optical properties of the tissue. The authors indicate that a "360° peritomy was performed on the conjunctiva", but peritomy alone, which is an incision on the conjunctiva at the corneoscleral limbus of the eye, is not sufficient to allow sufficient volume of the clarifying agent to reach the target tissue (in this case, the sclera). In order for this approach to be effective, a full surgical separation of the conjunctiva from the sclera is necessary, to allow the topical chemical agent to permeate into the interstitial space of the sclera.

One of the objects of this invention is to provide a method and apparatus for enhancing optical transmission through biologial tissues. Other objects of this invention will become apparent from the specifications, drawings, and by reference to the appended claims.

BRIEF DESCRIPTION OF DRAWINGS

Referring to the drawings.

DETAILED DESCRIPTION OF THE PREFERRED EMBODIMENTS

Figure 1:
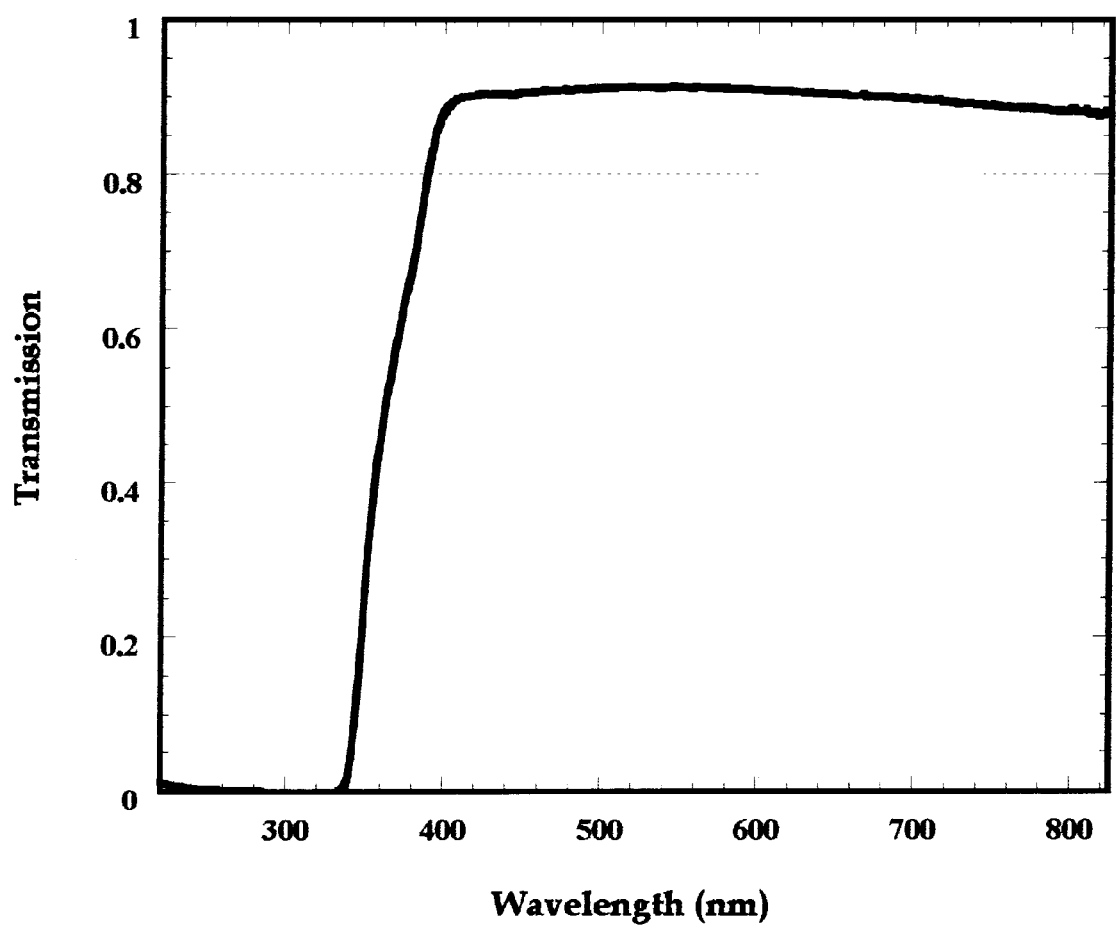
FIG. 1 illustrates the optical transmission characeristics of diatrizoate meglumine acid.

Optical transmission through biological tissue is one of the major challenges of all optical diagnostic and therapeutic modalities which are intended to access structures underlying the tissue surface. In diagnostics (e.g., imaging tissue structures with microscopes) the objects is to obtain clear image of imbedded structures, or signature optical information (e.g., spectroscopic information) from analytes in the blood stream or within the composition of biological tissues. Such images or optical information are distorted due to the attenuation of light, which is transmitted through, or reflected from, the tissue specimens.

In therapeutics (e.g., laser treatment of pigmented and vascular lesions) the goal is to selectively cause thermal necrosis in the target structures, without compromising the viability of surrounding tissues. The highly scattering medium of biological tissues, however, serves to diffuse the incident light, and causes thermal damage to tissues surrounding the target structures, impacting the selectivity of the procedure in destroying the target structures. It is therefore important to adopt a strategy which could minimize the optical attenuation of the overlying and surrounding tissues to treatment target structures, in order to minimize collateral tissue damage, and maximize the therapeutic effects at the target tissue.

When light is irradiated on biological tissues, there are several distinct mechanisms by which light is attenuated. The first attenuation stems from the mismatch of the index of refraction at the tissue interface. This index mismatch results in a reflection from the tissue surface, known as specular reflection. When the medium overlying tissue is air, this attenuation is on the order of 3–4%. Once light penetrates into the tissue, there are two mechanisms responsible for light attenuation: absorption and scattering. Attenuation mechanisms of tissue can be characterized by determining the optical properties of tissue.

The optical properties of tissue provide a practical basis for characterizing light propagation in this medium. The fundamental parameters which describe tissue optics are the absorption coefficient, $\mu_a$ (cm$^{-1}$), the scattering coefficient, $\mu_s$ (cm$^{-1}$), and the average cosine of the scattering angle associated with single scattering phase function, g. The probability that a photon is absorbed or conservatively scattered as it propagates in tissue, is given by the product of the path length of the photon, $\Delta s$, and the absorption and scattering coefficients, respectively. The phase function describes the probability, per unit solid angle, that a photon will be scattered into an angle $\Theta$. The average cosine of the phase function, g (also known as the anisotropy factor) provides a measure of the direction of scattering. Scattering is purely in the forward direction when g is 1 or $\Theta$ is 0°; the light is purely backscattered when g is −1, or $\Theta$ equals 180°. An isotropic scattering is specified by g equaling 0.

Most of the recent advances in modeling light-tissue interaction have been based on the radiative transport theory. The radiative transport theory provides a heuristic model that deals directly with the transport of power through turbid media. In this model, the distribution of light propagating through a turbid medium is given by the radiative transfer equation (Chandrasekar, 1960):

$$s \cdot \nabla L(r, s) = -(\mu_a + \mu_s)L(r, s) + \mu_s \int_{4\pi} p(s, s')L(r, s')d\omega' \quad (1)$$

where $\mu_a$ [cm$^{-1}$] is the absorption coefficient, $\mu_s$ [cm$^{-1}$] signifies the scattering coefficient p(s,s') [sr$^{-1}$] is the phase function representing the contribution of scattered light from the s' direction to s, and d$\omega$' denotes the differential solid angle in the s' direction. According to the radiative transport theory, the radiance L(r, s) [W m$^{-2}$ sr$^{-1}$] of light at position r travelling in the direction of the unit vector s is reduced due to absorption and scattering of the medium (first term on the right hand side of equation 1) and increased by the scattered contribution from s' to s direction (second term on the right hand side of equation 1). The phase function is generally assumed to be a function only of the angle between s and s'. Therefore p(s,s')=p(s·s')=p (cos $\Theta$). When the integral of the phase function is normalized to one, p(s,s') represents the probability density function for scattering from direction s' to s.

Even though in general the phase function varies from particle to particle, for most applications an approximate phase function is chosen such that the most important features of the scattering process are characterized. In isotropic media, the phase function is simply 1/(4$\pi$). In anisotropic media (such as most biological tissues), the average cosine of the phase function, g, is utilized to describe the degree of anisotropy of the medium:

$$g = \int_{4\pi} p(s \cdot s')(s \cdot s')d\omega \quad (2)$$

Scattering in a turbid medium is due to the heterogeneity of the refractive index of the constituent elements in the medium. The main constituent of tissue, water (by approximately 80%), has a refractive index of 1.33, whereas the refractive index of collagen is 1.45, and the refractive index of other constituents of tissue are also different from water, by a magnitude sufficient to result in a high level of optical scattering within the tissue. Any approach which serves to minimize this heterogeneity, will have a substantial impact on reducing the scattering within the tissue, leading to a higher optical transmission through the tissue.

One approach is by applying compression. In the case of sclera, for instance, a number of investigators have reported that when a fiberoptic contact probe is used to compress scleral tissue, the optical transmission through the sclera is increased. Vogel et al. (Vogel, Dlugos, Nuffer, Birngruber et al., 1991) have recently demonstrated that the difference in transmission diminishes with fiber contact if strong pressure is applied to the sclera. This increase in transmission due to fiber contact may be explained by the displacement of ground substance caused by the pressure of fiber tip. The thinning of the sclera and the reduction of the distance between collagen fibrils (due to the pressure exerted by the fiber) leads to changes in the interference of the light scattered from adjacent fibrils (Vogel et al., 1991). In this case, it is believed that more water than proteins and mucopolysaccharides are displaced, and that the concentration of the remaining ground substance increases and its refractive index becomes closer to that of the collagen fibrils, thereby reducing the heterogeneity of the refractive index of the constituents of the sclera. As a result, when a contact fiber is used to compress sclera, scattering is reduced, and consequently the transmission is increased. These effects are stronger when increased pressure is applied to the sclera (Cantor et al., 1989).

Another approach which has been used is the application of glycerol, topically, to enhance visualization through edematous corneas to allow adequate gonioscopic and ophthalmoscopic examinations. It has been long since known that glycerol applied topically in concentrations from 50% to 100% is effective in clearing edematous corneas, within two minutes following administration (Flood et al., 1989). It should be noted, however, that this method of applying hyperosmotic topical agents has been limited only to the cornea, and the prior art does not suggest such application for any other tissue type. Moreover, the method of topical administration of such chemical agents is ineffective in altering the optical properties of tissues other than the cornea, so long as the surface permeability barrier of tissue of the tissue (e.g., stratum corneum for the skin) is in place.

The present invention involves the application of a clarifying chemical agent to biological tissues, which are covered by a surface permeability barrier of tissue, in-vivo, ex-vivo, or in-vitro, for the purpose of augmenting the optical transmission through these tissues. While the basis of this effect has not been established definitively, in a number of experiments described below, it has been shown that optical transmission through tissues can be substantially enhanced, on a transient basis, using the topical administration of chemicals such as diatrizoate meglumine acid (commercially known as Hypaque®), glycerol, or glucose (hereinafter referred to as "clarifying agents"). It is possible that the tissue transport phenomena replace a portion of the tissue's water content with the above chemical agents, and the optical properties of these chemicals alter the bulk optical properties of the tissue such that the optical transmission through the tissue is increased. In time, the same transport phenomena replace these agents with water, restoring the tissue's original optical properties.

In the case of these clarifying agents, it is possible that the higher refractive index of these fluids (more than that of water, and closer to the refractive index of collagen and other constituents of tissue), leads to a reduction in the heterogeneity of refractive indices of the constituents of tissue, and therefore reduces the overall scattering of light as it is transmitted through the tissue. This method can be termed "interstitial refractive index matching", or IRIM.

Glycerol is a trihydric alcohol, a naturally occurring component of body fat. It is absorbed from the gastrointestinal tract rapidly, but at a variable rate. As such, topical administration of glycerol is not expected to cause any adverse effects, and should be a completely safe approach for altering the optical properties of tissues, prior to light irradiation.

Diatrizoate meglumine acid, which is commercially known as Hypaque®, is a radiographic injection solution. In the case of Hypaque®, the increased transmission through the tissue may be due to IRIM, or optical transmission characteristics which are superior to that of water, or a combination of both effects. In an experiment, a cuvette was filled with diatrizoate meglumine acid and its optical transmission characteristics were evaluated using a Varian CARY 5E™ UV-Vis-NIR spectrophotometer. The transmission characteristics were similar to that of a "high-pass filter", and the chemical exhibited very low transmission for wavelengths below approximately 400 nm, and very high transmission for wavelengths above 400 nm (see FIG. 1).

Experiments demonstrating the effects of IRIM are described below.

Relevant Experiments

A. In-Vitro Animal Experiments

Porcine eyes were enucleated immediately post-mortem, and were transported to the laboratory in a wet gauze pad, held at 4° C. during transport in a well-insulated cooler. Each eye was inflated with saline. Limbal conjunctiva and Tenon's capsule were dissected and excised using a pair of blunt Wescott scissors. A No. 64 Beaver blade was then used to outline 20 mm×20 mm sections of the sclera from the limbus to the equator of the globe. Incisions were deepened to the supra-choroidal space. Sections of sclera were then lifted off the intact choroid and ciliary body. Scleral thickness was measured and was determined to be 1.65 mm on average.

Three prepared sections of sclera were each then placed between quartz slides, and then between two flat aluminum plates. The tissue sample assembly was then fixed against the input port of a diffuse reflectance accessory (integrating sphere) of a Varian Cary 5E™ UV-Vis-NIR spectrophotometer, and diffuse transmission was measured for wavelengths ranging from 350 nm to 750 nm. The three tissue samples were then submerged in separate containers of glycerol, the first being submerged for 5 minutes, the second for 10 minutes, and the third for 15 minutes. Each sample was then again placed in the tissue assembly and was fixed against the input port of the diffuse reflectance accessory of the spectrophotometer, and the diffuse transmission was measured again over the same wavelength range as above. These measurements were also carried out, using three other scleral samples, and diatrizoate meglumine acid as the IRIM agent. The results for these measurements are shown in the FIGS. 2 (a–c), and 3 (a–c).

Figure 2:
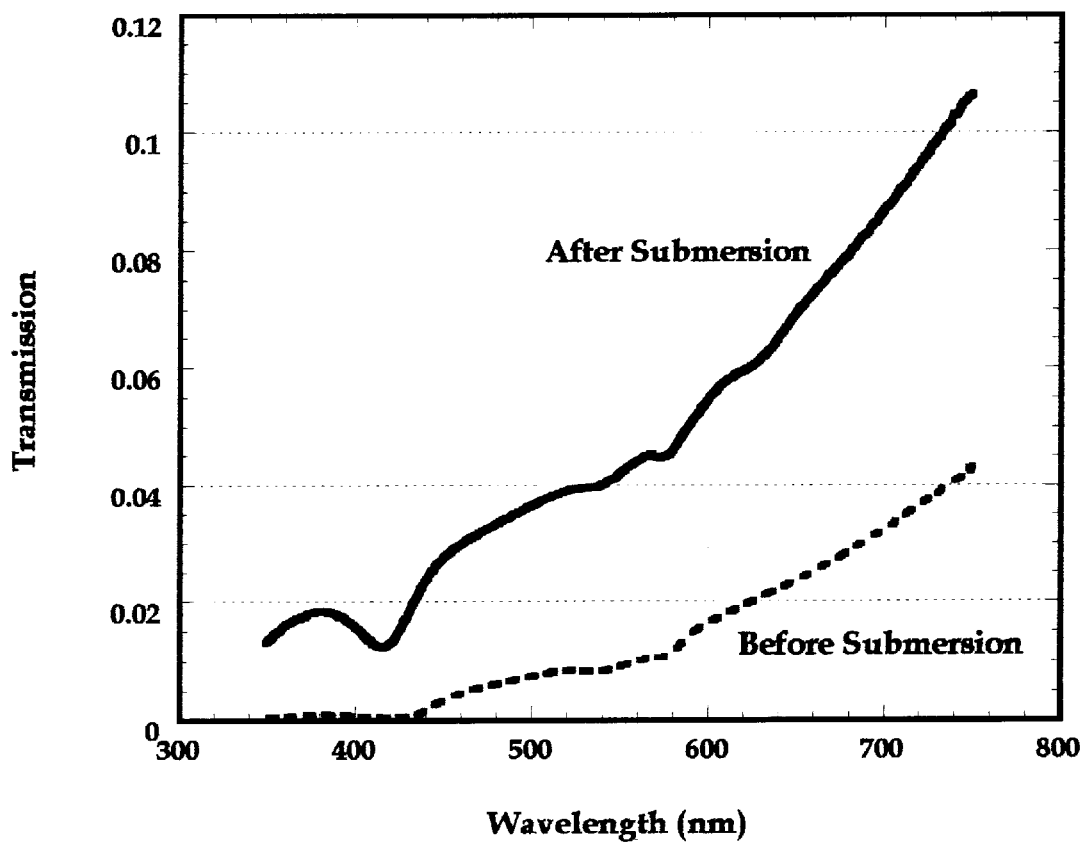
FIGS. 2(a), 2(b), and 2(c) illustrate the results of measurement of the diffuse transmission characteristics for porcine sclera, before and after submersion in glycerol, after 5, 10, and 15 minutes, respectively.
Figure 2:
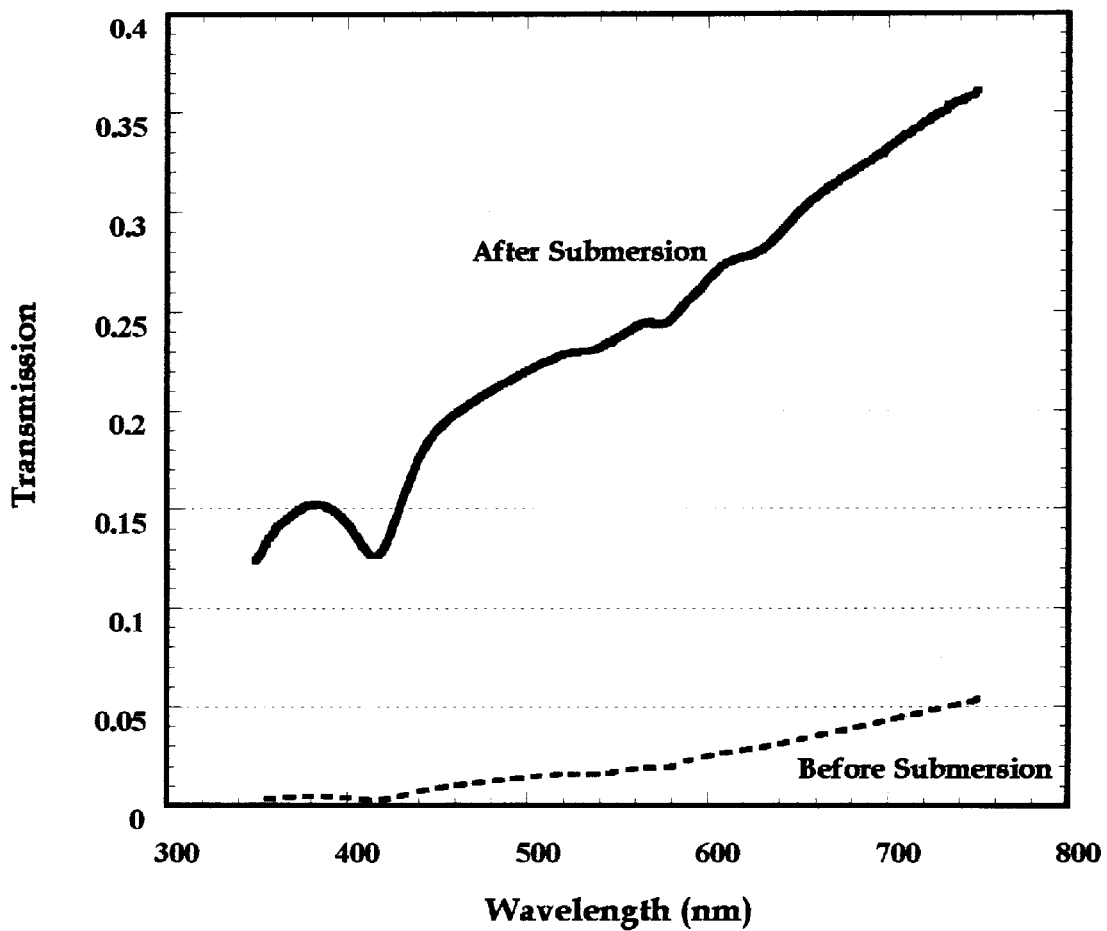
Figure 2C:
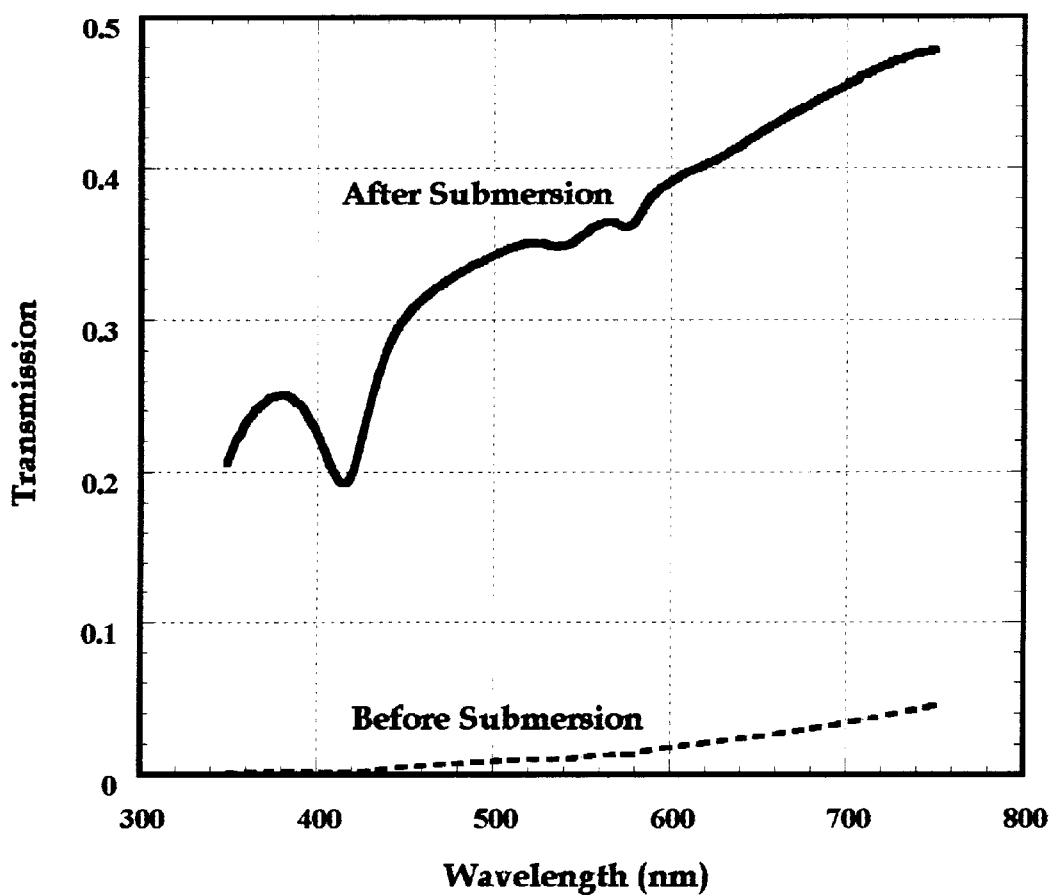
Figure 3:
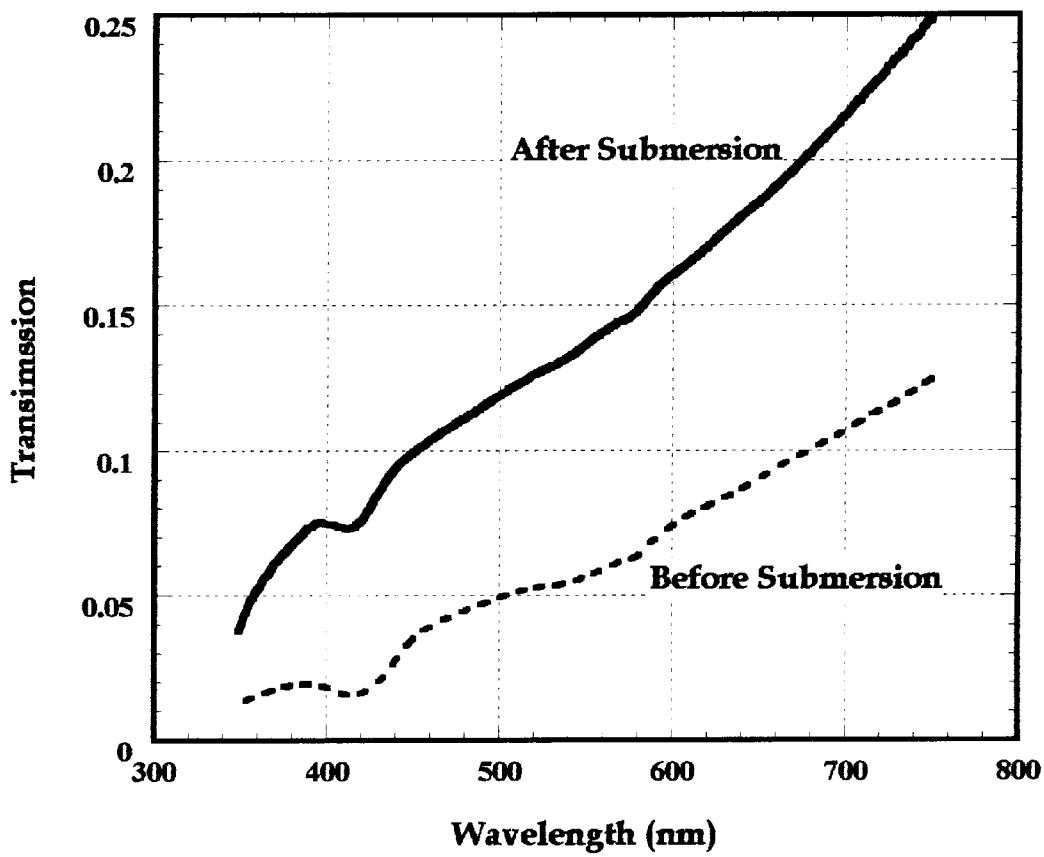
FIGS. 3(a), 3(b), and 3(c) illustrate the result of measurement of the diffuse transmission characteristics for porcine sclera, before and after submersion in diatrizoate meglumine acid, after 5, 10, and 15 minutes, respectively.
Figure 3:
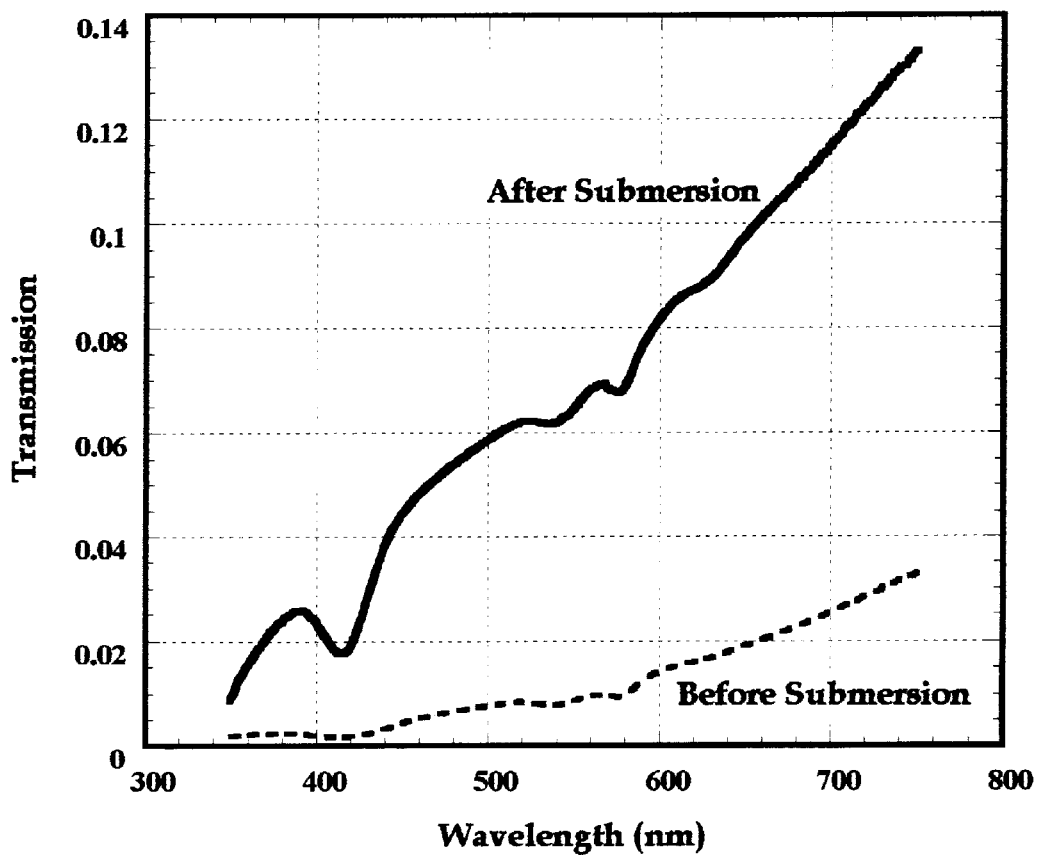
Figure 3:
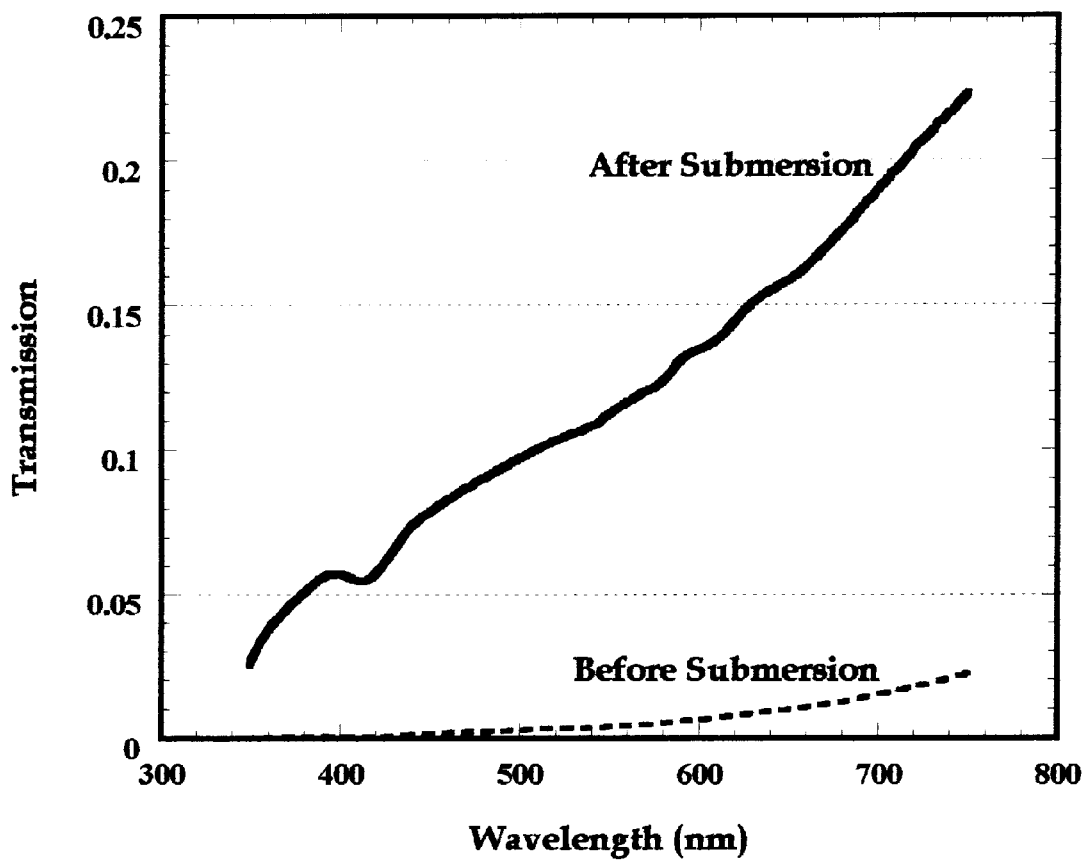

From the results shown in FIG. 2, it can be seen that the diffuse transmission through the sclera was increased by up to 240%, 660%, and 1090%, for samples which were submerged in glycerol for 5, 10, and 15 minutes respectively, with the most pronounced increase occurring at 750 nm wavelength (the longest wavelength for which measurements were carried out). Similarly, the results shown in FIG. 3 illustrate that the diffuse transmission through the sclera was increased by up to 200%, 395%, and 975%, for samples which were submerged in diatrizoate meglumine acid for 5,10, and 15 minutes respectively, with the largest increase occurring at 750 nm wavelength (the longest wavelength for which measurements were carried out). It is noteworthy that the samples became so transparent (grossly) that when placed against print, letters of the alphabet were clearly discernable through the tissue.

B. In-Vivo Animal Experiments

In order to assess the longitudinal effects of topical administration of glycerol or diatrizoate meglumine acid on the sclera, in-vivo experiments were carried out on two rabbits, and the eyes were examined for signs of inflammation once a day for approximately 1 week.

Each rabbit was put under anesthesia using an intramuscular injection of Rompin® and Ketamine®. The conjunctiva serves as the permeability barrier for the sclera, and therefore, the conjunctiva was surgically separated from the sclera and the distal surface of the sclera was exposed. Topical drops of glycerol were administered on one eye, and of diatrizoate meglumine acid in the contra-lateral eye, for both rabbits. In the case of glycerol, the sclera turned clear, almost instantaneously (in less than 5 seconds), whereas in the case of diatrizoate meglumine acid, the sclera turned clear in approximately 1 minute. The conjunctiva was stretched over the sclera, again, and stay sutures were used to re-attach the conjunctiva to the limbal region. Ocumycin® was administered topically to both eyes which had undergone surgery, to prevent infection. After approximately 5–10 minutes, the sclera in both eyes became opaque, again. Follow up examination on days 1, 3, and 5 showed no signs of inflammation on either eye.

C. In-Vivo Human Experiments

In order to investigate the applicability of the above method to the human model, and to skin tissue, additional experiments were carried out, using topical glycerol (99.9%, Mallinckrodt, Inc.) and diatrizoate sodium injection fluid, USP, 25% (Hypaque® Sodium, 25%, by Nycomed, Inc., Princeton, N.J.).

Two skin surfaces on the forearm were shaved and cleaned prior to measurements. A tape-strip method was used to remove the stratum corneum. Droplets of glycerol were then topically administered on one site, and droplets of the diatrizoate sodium injection fluid were administered on the second site, which was separated from the first site by 5 cm (a sufficient distance to ensure that the topical drug administered on one site does not interfere with the drug administered on the other site, through diffusion). The topical drugs administered formed an approximate circle of 1 cm in diameter. The drugs were left to diffuse into the tissue for approximately 8 minutes.

Surface reflectance measurements were made immediately after tape stripping of the skin (prior to topical administration of the drugs), and subsequently, approximately 8 minutes after topical administration of the drugs. A CSI Portable Diffuse Reflectance Spectrometer, developed by Canfield Scientific Instruments, Inc. (Fairfield, N.J.), was used for these surface measurements. This device is similar in standard absorption spectrometers, with the exception that the light source is a tungsten halogen lamp, and the sample chamber is replaced with a quartz fiber optic assembly. One leg of the bifurcated fiber optic bundle is coupled to the lamp and the other leg is coupled to the spectrometer. The joined end of the fiber bundle (approximately 3 mm in diameter) was placed in contact with the skin surface from which measurements were made. The measurements were made across a 330 nm to 840 nm spectral range, with a 0.5 nm resolution. The integration time for the measurements was set at 50 kHz.

Figure 4:
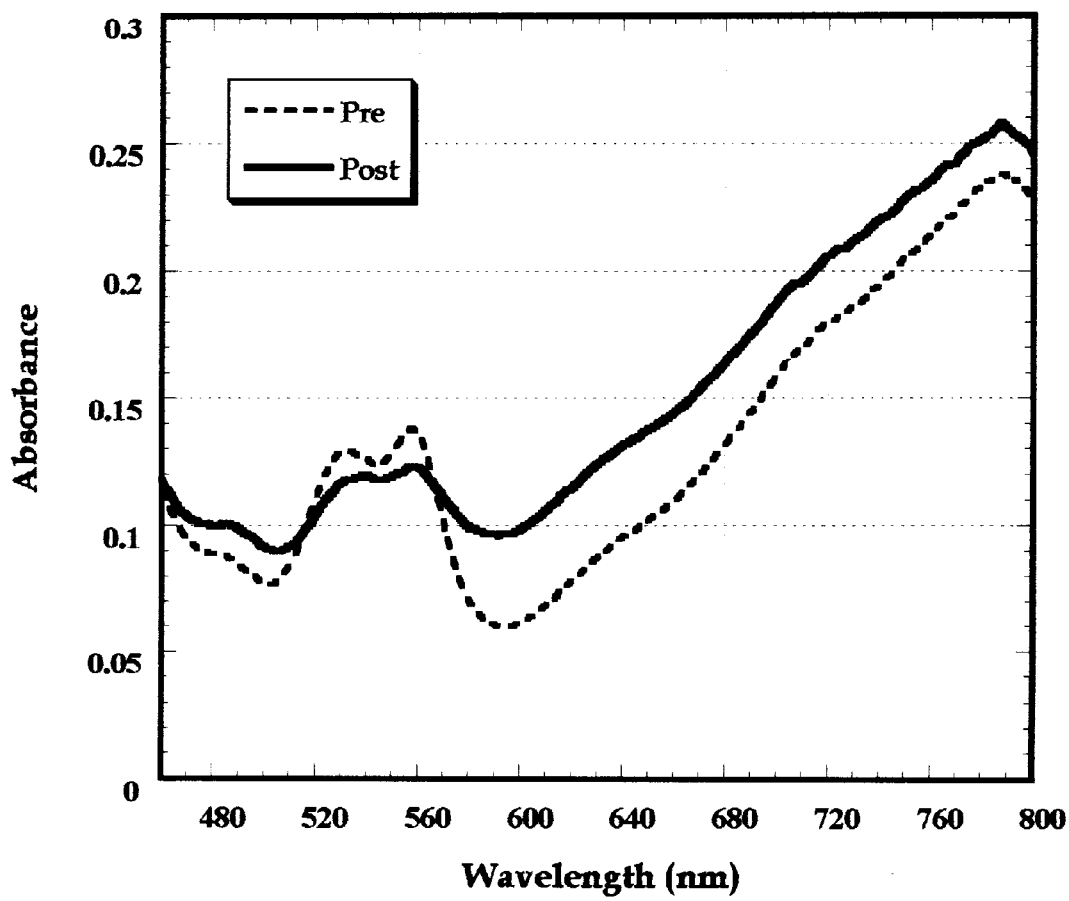
FIG. 4 illustrates the absorbance of human skin, in-vivo, immediately before and approximately 8 minutes after topical administration of glycerol, over a 460 nm to 800 nm spectral range.
Figure 5:
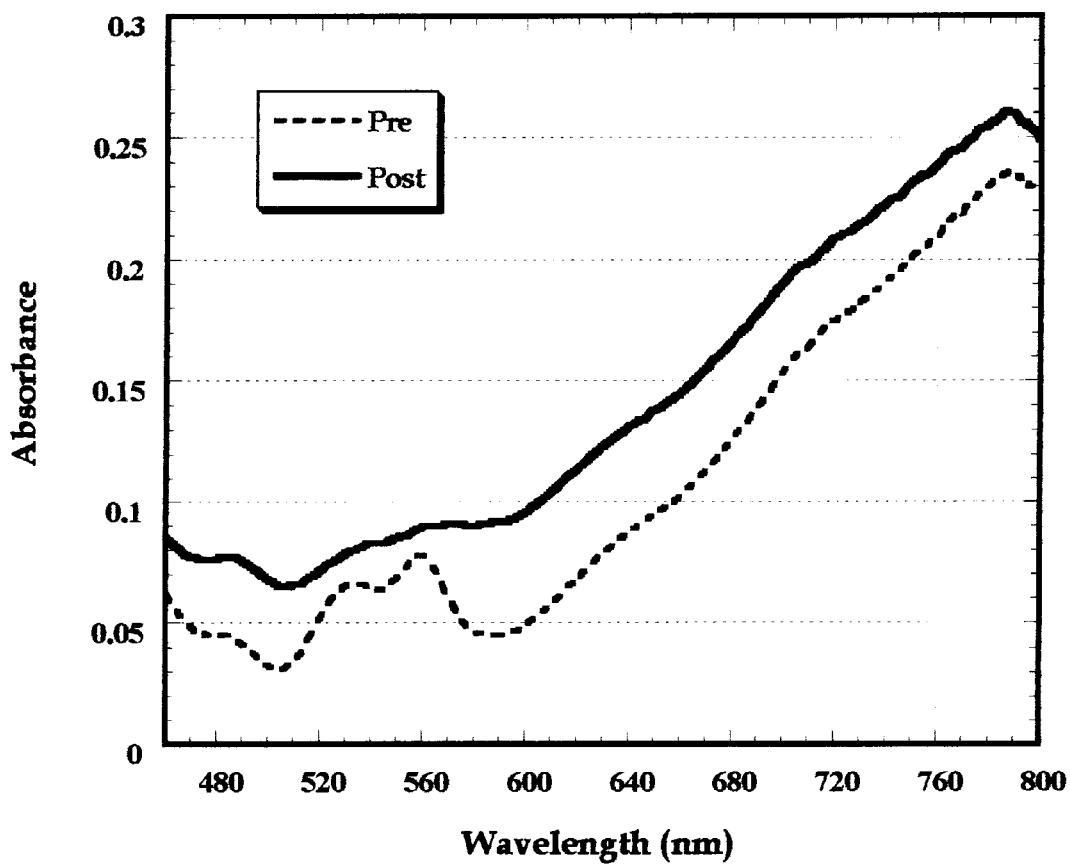
FIG. 5 illustrates the absorbance of human skin, in-vivo, immediately before and approximately 8 minutes after topical administration of diatrizoate sodium injection solution (25%), over a 460 nm to 800 nm spectral range.

FIGS. 4 and 5 illustrate the results from the above measurements. The data displayed in these graphs have been limited to a range of 480 nm to 800 nm to remove the portions of the spectra which were fraught with noise. The tape stripping of the skin causes a mild irritation of the skin, leading to a transient erythema. This erythema was noticed in both sites immediately after tape stripping, and subsided by the time the measurement after topical administration of the drug was made. As such, the spectra measured prior to topical administration of the drugs clearly demonstrate the higher concentration of blood immediately below the surface, as evidenced by the strong oxyhemoglobin peaks at approximately 530 nm and 560 nm.

FIGS. 4 and 5 demonstrate that the topical administration of glycerol and diatrizoate sodium injection solution, respectively, lead to an increase in absorbance of tissue, in-vivo, of up to 60.5% and 107% respectively. This increase in tissue-absorbance is believed to be caused by IRIM, leading to a reduction of the scattering of the superficial layers of the skin, thereby allowing a larger percentage of light to reach (and get absorbed by) the native chromophores of the skin (melanin and blood), thereby increasing the measured absorbance of the tissue.

It is important to note that further studies are necessary to optimize the above experiments. For instance, the tape-stripping method for removing the stratum corneum is generally unreliable in producing complete removal of this layer. Furthermore, the optimal diffusion time through human skin, for the above drugs, has not yet been determined. As such, the above experiments are only intended as a proof of principle for the use of IRIM in increasing transparency in human tissue, in-vivo. The results, while compelling, are not intended to demonstrate the full potential of this powerful technique in altering the optical properties of human tissue.

Apparatus Concept

The apparatus of the present invention comprises the following components: a) apparatus for bypassing the surface permeability barrier of tissue, such as the stratum corneum for the skin, or the conjunctiva for the eye; b) apparatus for topically or interstitially applying a chemical agent; and c) apparatus for delivery or collection of light for diagnostic or therapeutic purposes. Since each of these components consists of devices which are individually known to those skilled in the art, they are shown diagrammatically in FIG. 6. The preferred embodiment of this invention may be a combination of all three components, or different combinations of the above in twos.

In order for the topical chemical agent (e.g., glycerol) to affect the tissue stroma (i.e., below the surface layer), it is necessary for this substance to permeate through, or bypass, the surface permeability barrier of tissue. The stratum corneum is a sheet of essentially dead cells which migrate to the surface of the skin. It is well known that dry stratum corneum is relatively impermeable to water soluble substances, and it serves to maintain the hydration of the skin, by providing a barrier for evaporation of the water content of the skin, and also by serving as a barrier for fluids exterior to the body to diffuse into the skin.

Therefore, in order to allow a topically administered chemical agent to be transported into the skin, a strategy needs to be adopted to bypass the stratum corneum. Likewise, the conjunctiva of the eye needs to be bypassed, or surgically removed, for access to the sclera; the same is true for the epithelium of mucosal tissues. Hereinafter, this surface tissue layer will be referred to as the "surface permeability barrier of tissue", or SPBT, and the underlying tissue layer, as "covered biological tissue" or CBT.

In order to bypass the SPBT, and reach the CBT, a driving force can be applied to move molecules across the SPBT; this driving force can be electrical (e.g., iontophoresis, electroporation) or it may be physical, or chemical force, such as that provided by a temperature gradient, or a concentration gradient of a clarifying agent, or of a carrier agent (carrying clarifying agent) for increasing the permeability of the surface permeability barrier of tissue; alternatively, the driving force may be due to acoustic or optical pressures, as described by Weaver, et al. (Weaver, Powell, & Langer, 1991).

Figure 6:
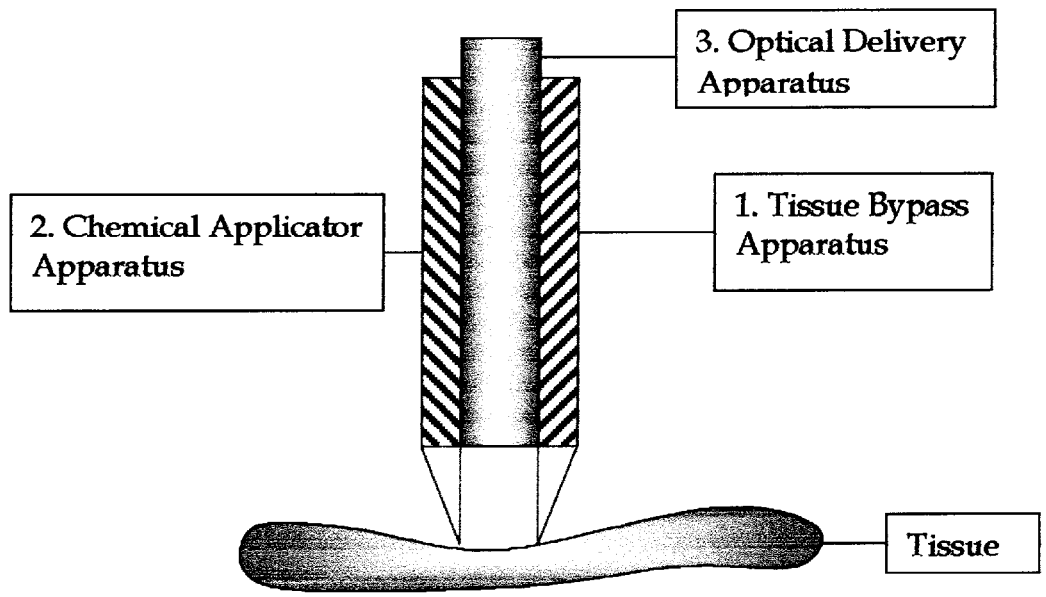
FIG. 6 illustrates diagrammatically a generalized system for bypassing surface permeability barrier of tissue, administering a topical chemical, and delivery of light.

In the case of the stratum corneum, one configuration for component 1 of FIG. 6 can be an electric pulse generator for inducing electroporation of the stratum corneum. This system, for instance, can be similar to the apparatus described by Prausnitz, et al.(Prausnitz et al., 1997).

Alternatively, component 1 may consist of a mechanical device with adhesive tape on the distal end, which may be brought in contact with the skin for tape stripping the stratum corneum. With each adhesion and detachment of the tape from the skin surface, a layer of the stratum corneum can be removed. The component may include means of advancing the tape with each application, so that a fresh tape surface can be used in each application.

More generally, component 1 may consist of a device which physically breaches the surface permeability barrier of tissue by abrasion, to expose the underlying tissue (CBT) which has a greater permeability. In the case of skin, this method is commonly known as dermabrasion.

Alternatively, component 1 may be an ablative solid state laser, such as any one of the following lasers: Er:YAG, Nd:YAG, Ho:YAG, Tm:YAG, Er.YSGG, Er:Glass, or an ablative semiconductor diode laser, such as a high-powered GaAs laser, or an ablative excimer laser, such as an ArFl or a XeCl laser. These lasers can be used to ablate the stratum corneum in its entirety with each pulse, over the surface area covered by the laser spot size. The short ablation depth of such lasers in human tissue (for instance, in the case of Er:YAG, an ablation depth on the order of 5–10 $\mu$m) allows for a rapid removal of the stratum corneum with each laser pulse.

Alternatively, component 1 may be an ultrasonic generator, causing poration of the stratum corneum, for instance as described by Kost (Kost et al., 1998). This approach is sometimes referred to as sonophoresis, or phonophoresis.

In yet an alternative configuration, component 1 may be a radiofrequency generator, selectively ablating a finite volume of the stratum corneum with each application, in a similar manner, for instance, as described by Manolis et al. (Manolis, Wang, & Estes, 1994) for ablation of arrhythmogenic cardiac tissues.

Alternatively, component 1 may be an iontophoresis system for drug delivery through the stratum corneum, for instance as described by Prausnitz, et al. (Prausnitz et al., 1997).

Alternatively, component 1 may be a microfabricated microneedle array, long enough to cross the SPBT, but not long enough to reach the nerve endings of the tissue, as that conceived, for instance, by the needle array developed by Henry et al. (Henry, McAllister, Allen, Prausnitz et al., 1998). The clarifying agent can be topically administered onto the SPBT and the microneedle array can then be inserted through the same surface permeability barrier of tissue. The insertion of the needle array will produce an array of apertures through the SPBT, which will then cause an increase in the permeation of the clarifying agent to the covered tissue (CBT).

Figure 7:
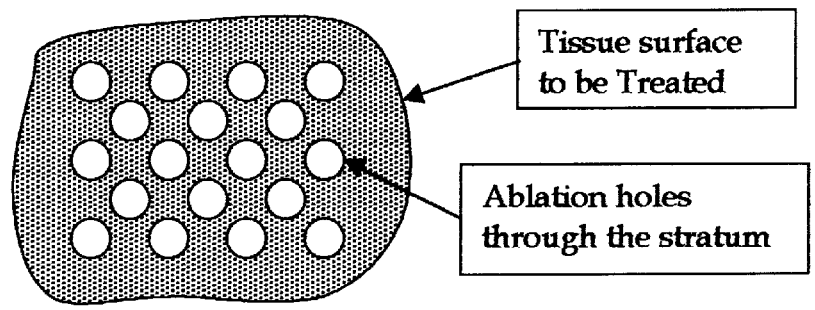
FIG. 7 illustrates diagrammatically a suggested pattern for removing the stratum corneum.

Alternatively, electrical arcing may be used to ablatethe SPBT. This may be done by an electrical generator that delivers electrical arcs at its delivery probe tip. Since stripping a large surface area of the stratum corneum, for instance, may be detrimental for the viability of the skin, the openings may be formed in an array of channels, or apertures, as shown in FIG. 7.

Finally, component 1 may be a dispenser for a chemical enhancer or carrier agent for transdermal drug delivery. In the case of the skin, for instance, it has long since been recognized that the permeability of tissue can be increased above its natural state by using penetrating solvents, which when combined with a drug and applied to the skin, greatly increase transdermal drug delivery. An example of one such chemical enhancer is dimethyl sulfoxide (DMSO). Other examples include different alcohols such as ethanol.

In the case of the conjunctiva, it is possible to surgically separate the conjunctiva from the sclera, prior to administration of the topical chemical. Component 1 can consist of a device to create a surgical flap of the conjunctiva, which can subsequently be sutured back onto the intact ocular tissues. Likewise, for the epithelium of mucosa, it is possible to use the same device to create openings in the underlying tissue.

For both the conjunctiva and the mucosa, all of the porative approaches (e.g., electroporation, ultrasonic poration, RF poration, microneedle array, chemical enhancement of trans-membrane delivery, or iontophoresis) may be used as component 1.

In yet another alternative configuration, the chemical may be injected interstitially, using an apparatus similar to a syringe with a hypodermic needle, in order to bypass the surface tissue layer. This approach is more invasive, but the apparatus may be simpler.

Component 2, in FIG. 6, is an applicator for administering the chemical topically. One possible configuration is a syringe, which dispenses the desired chemical over the tissue.

Finally, Component 3 of the overall system is the optical delivery or collection apparatus, which may be a fiberoptic probe (single or multi-fiber probe), or an articulated arm with specialized optics, depending on the optical delivery system, or optical imaging systems for image acquisition, such as a microscope.

Applications

Since virtually all diagnostic and treatment procedures in the field of biomedical optics involve the probing of light into biological media, the invention described here has broad applications across a wide range of optical procedures. The method described here essentially serves to augment optical penetration of biological tissues, whether for diagnostic or therapeutic purposes.

A. Diagnostics

The present method enhances any optical method that attempts to investigate objects or structures imbedded, or fluids within tissues, or analytes that exist within the blood or other biological fluids. Since this method serves to enhance transmission across a broad spectral range, it can be used in routine white-light microscopy to probe at focus planes underneath the surface. Alternatively, it could be used for spectroscopic (e.g., reflectance, fluorescence, or raman) information gathering.

For the same reason as above, this invention can be used for confocal microscopy to penetrate deep into the covered tissue, CBT, (e.g., on the order of millimeters) to examine a variety of cellular information, including cellular structures, imbedded tissue appendages, and various pigmented and non-pigmented lesions.

Optical coherence tomography (OCT), is a diagnostic method which relies on the reconstruction of scanned interferometric information from backscattered light from the tissue. This method is also limited in its resolution by the extent of optical penetration through the superficial layers, to probe imbedded objects. The present method could again serve to substantially augment the utility of OCT in investigating objects/structures imbedded in tissue.

Another application is the collection of fluorescence from fluorophores imbedded in tissue, as a diagnostic means of assessing presence or absence of biological parameters. The present method could enhance the signal to noise ratio of such a detection scheme.

Another application is in sensing of analytes within biological fluids in the tissue. For instance, the present invention may be used to non-invasively measure spectroscopic information from fluids such as the blood or interstitial fluid, in order to determine glucose concentration, or cholesterol level.

Another application for this method is in the use of other optical imaging methods for tumor detection, such as photon migration and optical tomography techniques.

Another application is in the use of photodynamic means of diagnosis of diseased/abnormal tissues. The depth of penetration of the activating light generally limits photodynamic methods. The preset invention will allow deeper penetration of visible-wavelength radiation for photodynamic activation.

Figure 8:
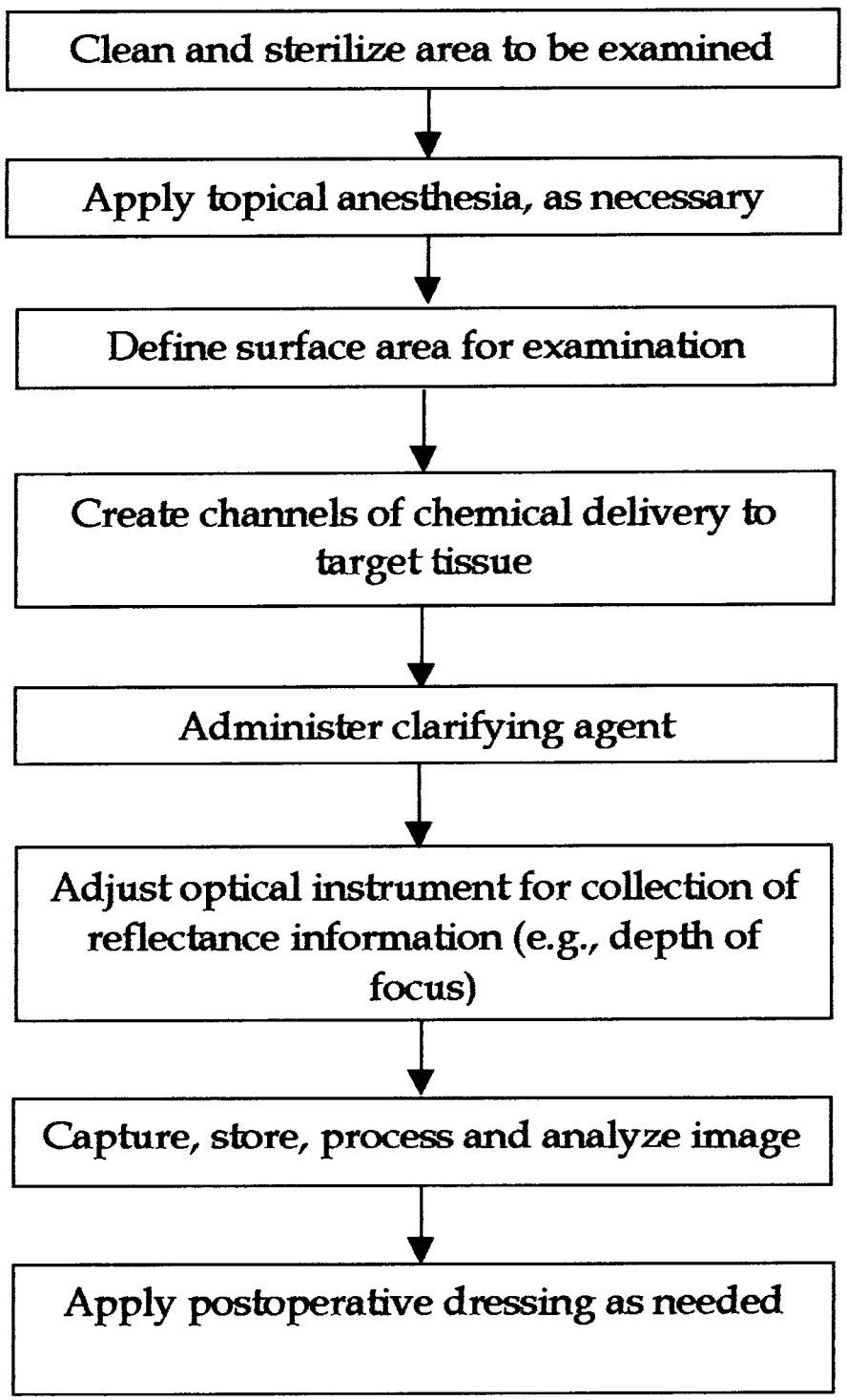
FIG. 8 is a flowchart of a diagnostic algorithm which can be carried out in accordance with the invention.

FIG. 8 illustrates a typical algorithm for applying the present invention for a diagnostic procedure.

B. Therapeutics

The present method is applicable to a wide array of therapeutic means involving imbedded objects in the tissue. In the field of ophthalmology, it encompasses all transscleral procedures, including transscleral cyclophotocoagulation, and transscleral retinopexy.

In the field of dermatology, applications include (but are not limited to) optical (or laser) targeting of all skin appendages, including the hair follicle (for permanent laser hair removal), pigmented and vascular lesions, tattoo removal, sebaceous glands (for acne treatment), subcutaneous fat (for optical liposuction), and eccrine glands (for permanent treatment of body odor).

The present method is applicable for photodynamic therapy of various cancerous tissues, augmenting the delivery of light to the photosensitizers bound to diseased tissues. As described above, the present invention significantly enhances the depth of penetration of light across a broad wavelength range.

Figure 9:
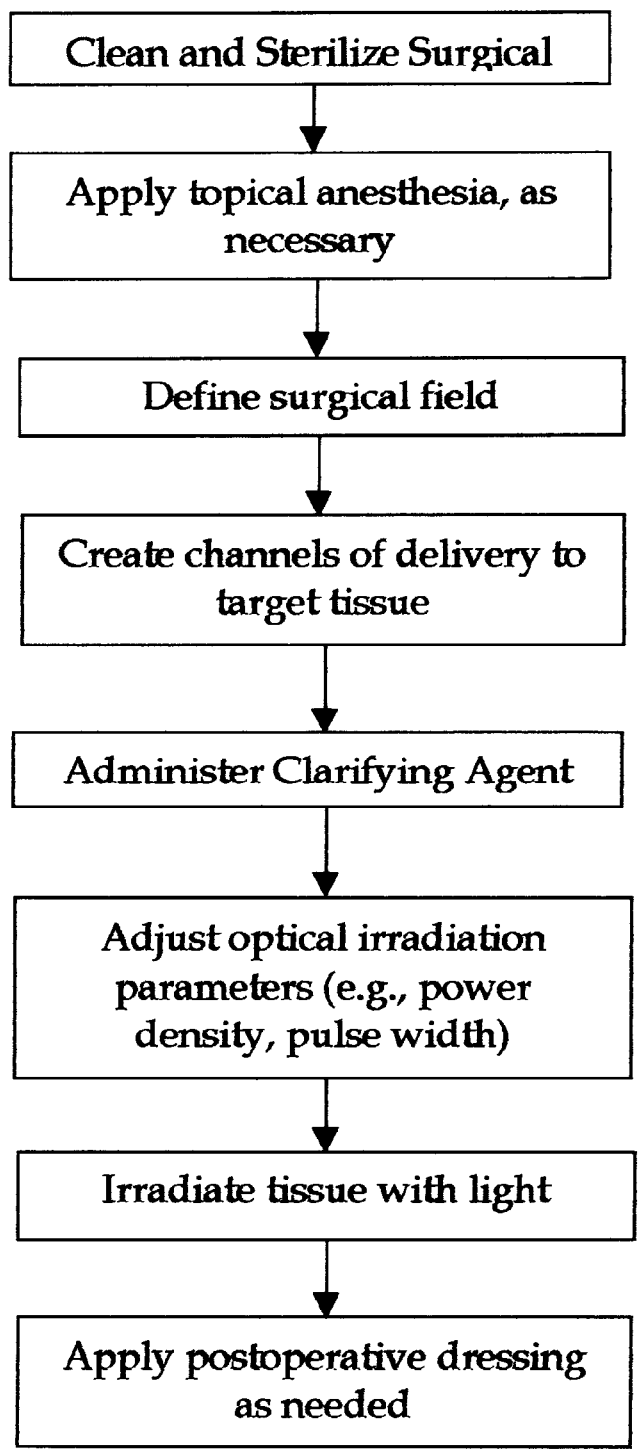
FIG. 9 is a flowchart of a treatment algorithm which can be carried out in accordance with the invention.

FIG. 9 illustrates a typical algorithm for applying the present invention to a therapeutic procedure.

Finally, the present invention also improves the efficacy of the diagnostic and therapeutic procedures, when energy sources from other segments of the electromagnetic spectrum are used (e.g., radiofrequency, and microwaves). Since IRIM also affects the overall elastic properties of tissues, acoustic signals travelling through tissue could also be affected, leading to a deeper penetration for ultrasonic waves for diagnostic and therapeutic purposes.

From the foregoing description, it will be apparent that I have invented a method and apparatus for enhancing optical transmission through biological tissues, underlying a surface permeability barrier of tissue. Variations and modifications of my invention will undoubtedly suggest themselves to those skilled in the art and will be within the scope of the invention. Thus the foregoing description should be taken as illustrative, rather than in a limiting sense.

References

1. McCarthy, J. J., Fairing, J. D., & Buchholz, J. C (Inventors). (Feb. 7, 1989). I. Tracor Northern (Assignee). *Confocal tandem scanning reflected light microscope.* (U.S. Pat. No. 4,802,748).
2. Lucas, F. F. (1930). The architecture of living cells—recent advances in methods of biological research—optical sectioning with the ultra-violet microscope. N.A.S.
3. Chan, K. F., Nemati, B., Rylander, I. H. G., & Welch, A. J. (1996). Chemically enhanced scleral transmission: a new approach for transscleral cyclophotogcoagulation. Proceedings of the Fourteenth Annual Houston Conference on Biomedical Engineering Research Houston.
4. Chandrasekar, S. (1960). *Radiative Transfer.* London, England: Oxford University Press.
5. Vogel, A., Dlugos, C., Nuffer, R., Birngruber, R. et.al. (1991). Optical Properties of human sclera and their significance for transscleral laser applications. *Laser Surg Med,* 11(4), 331–340.
6. Cantor, L. B., Nichols, D. A., Katz, L. J., Moster, M. R., Poryzees, E., Shields, J. A., & Spaeth, G. L. (1989). Neodymium-YAG transscleral cyclophotocoagulation. The role of pigmentation. *Investigative Ophthalmology and Visual Science,* 30(8),1834–1837.
7. Flood, T. P. et al. (1989). Hyperosmotic Agents. *Duane's Biomedical Foundation of Ophthalmology* (Vol. 3p. 5). Philadelphia: J. B. Lippencott Company.
8. Weaver, J. C., Powell, K. T., & Langer, R. S. Jr. (Inventors). (May 28, 1991). Massachussetts Institute of Technology (Assignee). *Control of transport of molecules across tissue using electroporation.* (U.S. Pat. No. 5,019, 034).
9. Prausnitz, M. R. et al. (1997). Reversible skin permeabilization for transdermal delivery of macromolecules. *Crit Rev Ther Drug Carrier Syst,* 14(4), 455–483.
10. Kost, J. et al. (1998). Phonophoresis. B. Berner, Dinh Steven M. et al. (Editors), *Electronically controlled drug delivery* (pp. 215–228). Boca Raton, FL: CRC Press, Inc.
11. Manolis, A. S., Wang, P. J., & Estes, N. A. 3. (1994). Radiofrequency catheter ablation for cardiac tachyarrhythmias. *Annals of Internal Medicine,* 121(6), 452–461.
12. Henry, S., McAllister, D. V., Allen, M. D., Prausnitz, M. R. et al. (1998). Microfabricated microneedles: a novel approach to transdermal drug delivery. *J. Pharm Sci,* 87(8), 922–925.

I claim:

1. Method for performing a diagnostic or therapeutic procedure on a first biological tissue having interstitial space therein and covered by a surface permeability barrier of a second tissue, said diagnostic and therapeutic procedure requiring optical access into said covered first biological tissue, said method comprising:

a) providing means for bypassing said surface permeability barrier of second tissue to permit the delivery of a clarifying agent past said surface permeability barrier of second tissue directly to said interstitial space within said covered first biological tissue, b) delivering said clarifying agent past said surface permeability barrier of second tissue directly to said interstitial space within said covered first biological tissue to enhance the optical transparency of said covered first biological tissue on a transient basis, c) performing said diagnostic or therapeutic procedure on said covered first biological tissue while the optical transparency thereof has been enhanced.

2. Method as in claim 1, wherein d) said diagnostic or therapeutic application is directed at affecting endogenous or exogenous structures or constituents within or underlying skin.

3. Method as in claim 2, wherein e) said endogenous structures within skin are sebaceous glands.

4. Method as in claim 2, wherein e) said endogenous structures within skin are hair follicles.

5. Method as in claim 2, wherein e) said endogenous structures within skin are eccrine glands.

6. Method as in claim 2, wherein e) said therapeutic application is directed to affecting subcutaneous fat.

7. Method as in claim 2, wherein e) said therapeutic application is directed at treating pigmented lesions of the skin.

8. Method as in claim 2, wherein e) said diagnostic application is directed at treating vascular lesions of the skin.

9. Method as in claim 2, wherein e) said diagnostic application is directed at light microscopy of said first biological tissue.

10. Method as in claim 2, wherein e) said diagnostic application is directed at confocal microscopy of said first biological tissue.

11. Method as in claim 2, wherein e) said diagnostic application is directed at optical coherence tomography of said first biological tissue.

12. Method as in claim 2, wherein e) said diagnostic application is directed at fluorescence spectroscopy of said first biological tissue.

13. Method as in claim 2, wherein e) said diagnostic application is directed at reflectance spectroscopy of said first biological tissue.

14. Method as in claim 2, wherein e) said diagnostic application is directed at non-invasive analyte sensing.

15. Method as in claim 2, wherein e) said diagnostic application is directed at measuring the glucose concentration in blood.

16. Method as in claim 2, wherein e) said diagnostic application is directed at measuring the glucose concentration in interstitial fluids.

17. Method as in claim 2, wherein
e) said diagnostic application is directed at measuring cholesterol concentration in blood.

18. Method as in claim 2, wherein
e) said diagnostic application is directed at optical tomography of said first biological tissue.

19. Method as in claim 2, wherein
e) said diagnostic application is directed at photodynamic detection of abnormal said first biological tissue.

20. Method as in claim 1, said interstitial space having interstitial fluid within said said interstitial space, wherein:
d) said clarifying agent alters the refractive index of said interstitial fluid on a transient basis to reduce the heterogeneity of the refractive indices within said interstitial space thereby to reduce the level of optical scaterring within said first covered biological tissue.

* * * * *